United States Patent [19]

Seha

[11] 4,065,478
[45] Dec. 27, 1977

[54] PROCESS FOR THE MANUFACTURE OF α,α'-AMINONITROANTHRAQUINONES

[75] Inventor: Zdenek Seha, Basel, Switzerland

[73] Assignee: Ciba-Geigy AG, Basel, Switzerland

[21] Appl. No.: 640,372

[22] Filed: Dec. 15, 1975

[30] Foreign Application Priority Data

Dec. 19, 1974 Switzerland .................. 16978/74

[51] Int. Cl.$^2$ .................................. C07C 97/24
[52] U.S. Cl. .................................. 260/382
[58] Field of Search .................................. 260/382

[56] References Cited

U.S. PATENT DOCUMENTS

| | | | |
|---|---|---|---|
| 1,255,719 | 2/1918 | DuToit | 260/382 |
| 3,881,865 | 5/1975 | Greenhalgh et al. | 260/378 X |
| 3,933,867 | 1/1976 | Thiem et al. | 260/382 |
| 3,969,374 | 7/1976 | Thiem et al. | 260/382 |

*Primary Examiner*—Paul F. Shaver
*Attorney, Agent, or Firm*—Burgess, Dinklage & Sprung

[57] ABSTRACT

A process for the manufacture of α,α'-aminonitroanthraquinones, from α,α'-dinitroanthraquinones, wherein the α,α'-dinitroanthraquinones are reacted with ammonia in dipolar aprotic solvents which are inert to ammonia, the reaction substrates and reaction products.

10 Claims, No Drawings

PROCESS FOR THE MANUFACTURE OF α,α'-AMINONITROANTHRAQUINONES

The present invention provides a process for the manufacture of α,α'-aminonitroanthraquinones from α,α'-dinitroanthraquinones which comprises reacting α,α'-dinitroanthraquinones with ammonia in dipolar aprotic solvents which are inert to ammonia, the reaction substrates and reaction products.

The reaction takes place according to the general reaction equation

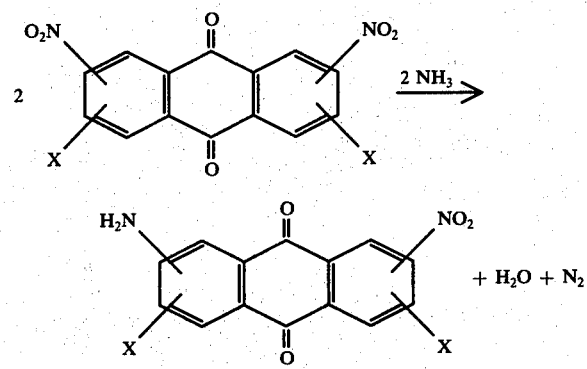

wherein X represents hydrogen or a functional substituent, for example the carboxyl, sulpho, lower alkyl or halogen group, which can be attached to the anthraquinone nucleus direct or through a bridge member. Advantageously X represents hydrogen.

The α,α'-aminonitroanthraquinones obtained by the process according to the invention are known and constitute useful dyestuff intermediates.

Processes for the manufacture of the α,α'-aminonitroanthraquinones as defined herein are already known. However, these are without exception more complicated reduction or substitution processes. In addition, these known processes result in inhomogeneous products or product mixtures.

Thus, for example, various processes are disclosed in German Pat. No. 76262 for manufacturing "partial" reduction products of dinitroanthraquinones. However, according to the particulars of this patent specification, these products are not homogeneous, "but a mixture of unchanged dinitroanthraquinone, diamidoanthraquinone and other compounds which are very difficult to separate and have therefore not been investigated more closely (inter alia also nitroamidoanthraquinones)".

German Pat. No. 78772 also discloses a process for the manufacture of nitroamidoanthraquinones by heating dinitroanthraquinones with bisulphites of alkalies or alkaline earth metals. Apart from the fact that the particulars disclosed therein are incomplete in many respects, an experimental verification of the example that serves to illustrate the process shows that, under these conditions, only traces of nitroamidoanthraquinones result, and that the main product of the reaction consists rather of diamidoanthraquinone.

German Pat. Nos. 473.871 and 147.851 disclose, for example, reduction processes in which hydrogenated bases of the quinoline series or aromatic mono- or dialkylamines are used as reducing agents. The compounds obtained, however, probably also constitute product mixtures or inhomogeneous products, since they have melting points which are approximately 20° below the true melting points of the desired compounds.

The novel process according to the invention makes it possible to obtain in simple manner α,α'-aminonitroanthraquinones from the corresponding α,α'-dinitroanthraquinones, since surprisingly virtually only one nitro group in α-position is reacted selectively when using gaseous ammonia and a solvent as defined herein at the preferred reaction temperatures. The reaction products are obtained in high purity by a special separation method. The reaction conditions are simple and the reaction course is easily kept under control. No problems regarding corrosion or of a technical nature arise in respect of the apparatus used and the recovery of the solvents employed presents no difficulties. Almost no residues occur during the reaction, so that the novel process marks a considerable advance, particularly from the ecological standpoint.

After the ammonolysis the solvent employed can be regenerated almost completely by simple distillation, or else it is recycled without treatment.

Examples of α,α'-aminonitroanthraquinones which can be manufactured by the process according to the invention are: 1,5-aminonitroanthraquinone, 1,8-aminonitroanthraquinone, the sodium salt of 1,8-aminonitroanthraquinone-6/7-sulphonic acid, 1,5-aminonitro-2-methylanthraquinone, and 1,5-aminonitro-2-chloroanthraquinone.

The pure products isolated by simple separation methods after the ammonolysis were examined for their identity and purity by infra-red mass spectroscopy, titrimitry and ultimate analysis. The following melting points were identified in the pure products:

1,5-aminonitroanthraquinone: 299° to 302° C.
1,8-aminonitroanthraquinone: 305° to 308° C.

The ammonolysis is carried out in ordinary reaction vessels or autoclaves. A suitable apparatus is the rotary evaporator or, for batches produced on an industrial scale, the paddle drier (Venuleth). The reaction temperature will be at least 60° C. The preferred reaction temperature is between 100° and 130° C. The upper temperature range is in the region of 180° C; but at higher temperatures the selectivity of the ammonolysis decreases. The ammonolysis can be carried out both under pressure and without pressure. It is preferred to operate without pressure. The reaction time is from 0.5 to 15 hours, preferably from 1 to 8 hours.

The weight ratio of the dipolar aprotic solvent as reaction medium to the dinitroanthraquinone is advantageously between 4:1 to 10:1.

As reagent, the ammonia is normally passed into the reaction medium in gaseous form. The amounts of ammonia to be used are advantageously somewhat above the stoichiometric requirement. However, the excess of ammonia is usually only about 50%, referred to the required stoichiometric amount.

As especially suitable solvents which can be used according to the invention there may be mentioned dipolar aprotic solvents which contain —SO₂— or —SO— groups and have a dielectric constant of at least 30, for example open-chain or cyclic low molecular sulphones of formula

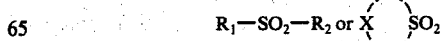

wherein each of $R_1$ and $R_2$ is a straight-chain or branched alkyl group of 1 to 4 carbon atoms, and X is a straight or branched hydrocarbon chain of 4 to 10 atoms. Examples of such sulphones are dialkyl sulphones, e.g. dimethyl sulphone, methyl ethyl sulphone, diethyl sulphone, methyl-n-propyl sulphone, methyl isopropyl sulphone, methyl-n-butyl sulphone, ethyl isobutyl sulphone, methyl-(1-methylbutyl)-sulphone, diisopropyl sulphone; alkylenesulphones, e.g. tetramethylenesulphone, 3-methyl-tetramethylenesulphone, pentamethylenesulphone, hexamethylenesulphone; alkylsulphonyl compounds, for example bis-(alkylsulphonyl)-alkanes, e.g. bis-(methylsulphonyl)-methane, bis-(ethylsulphonyl-methane, bis-(ethylsulphonyl)-dimethylmethane, and mixtures of the above solvents. It is preferred to use tetramethylenesulphone.

Suitable solvents are also those that contain a tertiary acid amide group, for example dimethyl formamide, dimethyl acetamide, tetramethylurea etc.

The $\alpha,\alpha'$-aminonitroanthraquinones are obtained in high purity by recrystallising the crude reaction products from 40–80%, preferably from 65%, sulphuric acid.

The following Examples illustrate the method of carrying out the process according to the invention but imply no restriction to what is described therein. The parts are by weight.

EXAMPLE 1

29.8 parts of 1,5-dinitroanthraquinone and 260 parts of tetramethylenesulphone are heated to 120° C in a flask (to which advantageously a rotary evaporator is attached) and gaseous ammonia is bubbled into the suspension. The water of reaction is continuously distilled off and removed. The nitrogen evolved is expelled by introducing fresh ammonia. When the reaction is terminated (complete reaction is achieved after 6 to 7 hours), the tetramethylenesulphone is completely distilled off in vacuo. The residue (26 parts) has the following composition:
  70.5% of 1-amino-5-nitroanthraquinone
  23.7% of 1,5-diaminoanthraquinone
  3.1% of 5-nitro-1-hydroxyanthraquinone and
  2.7% of 1-amino-5-hydroxyanthraquinone.

SEPARATION METHOD

The residue is dissolved in 259 parts of 98% sulphuric acid. The solution is diluted with 131 parts of water and filtered at 120° C, to leave as residue 0.8 part of undissolved 5-nitro-1-hydroxyanthraquinone. The filtrate is cooled and the crystallised product is filtered off. The filter cake is washed with cold 65% sulphuric acid (acid filtrate), then suspended in cold water and washed neutral. The filter cake is subsequently washed with hot, approximately 2% potassium hydroxide solution (alkaline filtrate A) and with hot water and dried. The 1-amino-5-nitroanthraquinone obtained (16.3 parts) is very pure and melts at 299° to 302° C. The acid filtrate is then diluted with water in the ratio 1:3 and the precipitate that has formed is filtered off and washed neutral. The filter cake is then washed neutral with hot, approximately 2% potassium hydroxide solution (alkaline filtrate B) and hot water and dried. Yield: 8.2 parts of a mixture of 6.2 parts of 1,5-diaminoanthraquinone and 2 parts of 1-amino-5-nitroanthraquinone.

It is also possible to isolate 0.7 part of 1-amino-5-hydroxyanthraquinone from the alkaline filtrates A and B. Very pure products are obtained by this separation method. The selectivity of the reaction in respect of 1-amino-5-nitroanthraquinone is 68.2%.

EXAMPLE 2

29.8 parts of 1,8-dinitroanthraquinone in 260 parts of tetramethylenesulphone are reacted in a flask as in example 1 for 5 to 6 hours at 110° C. After the reaction is terminated, the residue, consisting of 91.4% of 1-amino-8-nitroanthraquinone, 4.1% of 1,8-diaminoanthraquinone, 2.3% of 1-nitro-8-hydroxyanthraquinone and 2.2% of 8-amino-1-hydroxyanthraquinone, is separated as already described, to yield pure 1,8-aminonitroanthraquinone which melts at 305°–308° C. The selectivity of the reaction in respect of the desired 1-amino-8-nitroanthraquinone is 90.7%.

EXAMPLE 3

The procedure of Example 2 is repeated with the same batch and under the same conditions. However, the introduction of ammonia is interrupted after 2 hours and the tetramethylenesulphone is distilled off. The residue (26.8 parts) has the following composition:
  78.3% of 1-amino-8-nitroanthraquinone
  16.4% of 1,8-dinitroanthraquinone
  3.4% of 8-nitro-1-hydroxyanthraquinone and
  1.9% of 1-amino-8-hydroxyanthraquinone.

In this case the reaction mixture contains no 1,8-diaminoanthraquinone and the separation of pure 1-amino-8-nitroanthraquinone is easier.

SEPARATION METHOD

The reaction residue is dissolved in 176 parts of 89% sulphuric acid. The solution is diluted with 89 parts of water and filtered at 120° C. The residue consists of 5.3 parts of a mixture of 4.4 parts of 1,8-dinitroanthraquinone and 0.9 part of 8-nitro-1-hydroxyanthraquinone as filter cake. 8-Nitro-1-hydroxyanthraquinone can be removed from this mixture with dilute hot potassium hydroxide solution and the residual 1,8-dinitroanthraquinone used again in the reaction.

The filtrate is diluted with water in the ratio 1:3 and the precipitate that has formed is filtered off and washed neutral with water. The filter cake obtained is then washed neutral with hot, approximately 2% potassium hydroxide solution and hot water and dried. Yield: 21 parts of 1-amino-8-nitroanthraquinone. The product is very pure and melts at 305°–308° C. It is possible to isolate 0.5 part of 1-amino-8-hydroxyanthraquinone in addition from the alkaline filtrate.

The total reaction in Example 3 is 85.2% and the selectivity is 93.5%. The reaction selectivity to yield 1,8-aminonitroanthraquinone can therefore be increased by systematically shortening the reaction time, but the reaction is incomplete.

I claim:
1. A process for the manufacture of $\alpha,\alpha'$-aminonitroanthraquinone from an $\alpha,\alpha'$-dinitroanthraquinone with a selectivity of at least about 70% comprising the step of reacting an $\alpha,\alpha'$-dinitroanthraquinone with ammonia in a dipolar aprotic solvent which is inert to ammonia, the reaction substrate and the reaction product said ammonia being present in excess of, at most, about 50% over the stoichiometric amount.

2. A process according to claim 1 which comprises the use of a dipolar aprotic solvent which contain a —SO$_2$— or —SO— group.

3. A process according to claim 2 which comprises the use of a dipolar aprotic solvent of formula

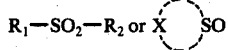

wherein each of $R_1$ and $R_2$ is a straight-chain or branched alkyl group of 1 to 4 carbon atoms and X is a substituted or unsubstituted, straight or branched hydrocarbon chain of 4 to 10 carbon atoms.

4. A process according to claim 3 which comprises the use of tetramethylensulphone as solvent.

5. A process according to claim 1 which comprises the use of solvent which contains a tertiary acid amide group.

6. A process according to claim 1 which comprises the use of gaseous ammonia.

7. A process according to claim 1, wherein the reaction is carried out at a temperature between 60° and 180° C.

8. A process according to claim 7, wherein the reaction is carried out at a temperature between 100° and 130° C.

9. A process according to claim 1, comprising the further step of recrystallising the $\alpha,\alpha'$-aminonitroanthraquinone from 40 to 80% sulphuric acid.

10. A process according to claim 9 wherein said recrystallizing is effected from 60 percent sulphuric acid.

* * * * *